US012594189B2

(12) United States Patent
    Fösel

(10) Patent No.: US 12,594,189 B2
(45) Date of Patent: Apr. 7, 2026

(54) LONG-TERM MONITORING OF THE INCISION PERFORMANCE OF AN OPHTHALMIC LASER SURGICAL SYSTEM

(71) Applicant: Alcon Inc., Fribourg (CH)

(72) Inventor: Matthias Fösel, Memmelsdorf (DE)

(73) Assignee: ALCON INC., Fribourg (CH)

( * ) Notice: Subject to any disclaimer, the term of this patent is extended or adjusted under 35 U.S.C. 154(b) by 325 days.

(21) Appl. No.: 18/457,055

(22) Filed: Aug. 28, 2023

(65) Prior Publication Data

US 2024/0074904 A1    Mar. 7, 2024

Related U.S. Application Data

(60) Provisional application No. 63/374,434, filed on Sep. 2, 2022.

(51) Int. Cl.
    *A61F 9/008*        (2006.01)

(52) U.S. Cl.
    CPC .. *A61F 9/0084* (2013.01); *A61F 2009/00844* (2013.01); *A61F 2009/00855* (2013.01); *A61F 2009/00897* (2013.01)

(58) Field of Classification Search
    CPC .......... A61F 9/0084; A61F 2009/00844; A61F 2009/00855; A61F 2009/00861; A61F 2009/00897
    USPC .......................................................... 606/4
    See application file for complete search history.

(56) References Cited

U.S. PATENT DOCUMENTS

| | | | |
|---|---|---|---|
| 7,584,756 B2 | 9/2009 | Zadoyan | |
| 2007/0173796 A1* | 7/2007 | Kessler | ................... A61F 9/008 606/10 |
| 2010/0130966 A1* | 5/2010 | Brownell | ................ A61F 9/008 606/4 |
| 2011/0245817 A1* | 10/2011 | Yokosuka | ........... A61F 9/00821 606/4 |
| 2012/0080586 A1 | 4/2012 | Deisinger | |
| 2016/0325375 A1 | 11/2016 | Lemonis | |
| 2021/0052425 A1* | 2/2021 | Knox | ................... B29D 11/023 |
| 2022/0015949 A1* | 1/2022 | Vankov | ................ G02B 26/101 |
| 2023/0165717 A1* | 6/2023 | Khatibzadeh | ....... A61F 9/00836 606/5 |

\* cited by examiner

*Primary Examiner* — Ahmed M Farah

(57)        ABSTRACT

An ophthalmic surgical system for monitoring incision performance includes a laser device, a camera, and a computer. laser device delivers a laser beam with a laser setting energy towards a target to create optical breakdowns in the target. The camera generates images of the optical breakdowns in the target. The computer instructs the laser device to create the optical breakdowns in the target to yield a test pattern. The test pattern comprises regions of optical breakdowns, where each region was created with a different laser setting energy. From the images, the computer identifies a lowest energy region with substantially continuous optical breakdowns, and designates the laser setting energy used to create the identified region as a threshold energy.

19 Claims, 4 Drawing Sheets

PATTERN
50a

REGIONS
54a

E1　E2　E3　E4　E5　E6　E7

INCREASING ENERGY

PATTERN
50b

REGIONS
54b

INCREASING
ENERGY

LONG-TERM MONITORING OF THE INCISION PERFORMANCE OF AN OPHTHALMIC LASER SURGICAL SYSTEM

TECHNICAL FIELD

The present disclosure relates generally to ophthalmic laser surgical systems, and more particularly to long-term monitoring of the incision performance of an ophthalmic laser surgical system.

BACKGROUND

Certain ophthalmic laser surgical systems include a femtosecond laser that creates photodisruptions in tissue to form incisions. To create the photodisruptions, the laser directs laser pulses with an energy selected using a laser setting. If the laser setting energy meets (e.g., is at or above) a threshold energy, the pulse creates a photodisruption. For safety, the photodisruptions should be created with the lowest feasible amount of energy.

The energy yielded from a specific laser setting is tested during manufacture of the system and initial inspection of the system. However, laser surgical systems change over their service life such that a greater laser setting energy may be needed to meet the threshold energy.

BRIEF SUMMARY

In certain embodiments, an ophthalmic surgical system for monitoring incision performance includes a laser device, a camera, and a computer. The laser device delivers a laser beam with a laser setting energy towards a target to create optical breakdowns in the target. The camera generates images of the optical breakdowns in the target. The computer instructs the laser device to create the optical breakdowns in the target to yield a test pattern. The test pattern comprises regions of optical breakdowns, where each region was created with a different laser setting energy. From the images, the computer identifies a lowest energy region with substantially continuous optical breakdowns, and designates the laser setting energy used to create the identified region as a threshold energy.

Embodiments may include none, one, some, or all of the following features: The substantially continuous optical breakdowns is defined as at least 90% of the pulses formed an optical breakdown. The computer accesses a previous test pattern comprising previous regions of previous optical breakdowns, and compares the test pattern with the previous test pattern to detect a change in threshold energy. The previous test pattern may have been created more than one month ago. The regions of the test pattern may be arranged substantially similarly to the previous regions of the previous test pattern such that each region has a corresponding previous region in the same location. For each region, the laser setting energy that created the region may be substantially the same as the laser setting energy that created the previous region corresponding to the region. The computer may: provide a notification of the change in the threshold energy; adjust the laser setting energy to compensate for the change in the threshold energy; and/or extrapolate from the test pattern and the previous test pattern to predict a future threshold energy. Each region of the test pattern has a substantially rectangular shape. Each region of the test pattern has a substantially triangular shape.

In certain embodiments, a method for monitoring incision performance includes instructing, by a computer, a laser device to deliver a laser beam with a laser setting energy towards a target. The laser beam creates optical breakdowns in the target to yield a test pattern, where the test pattern comprises regions of optical breakdowns, each region created with a different laser setting energy. The method also includes generating, by a camera, images of the optical breakdowns in the target; identifying, by the computer, from the images a lowest energy region with substantially continuous optical breakdowns; and designating, by the computer, the laser setting energy used to create the identified region as a threshold energy.

Embodiments may include none, one, some, or all of the following features: The substantially continuous optical breakdowns is defined as at least 90% of the pulses formed an optical breakdown. The method also includes: accessing, by the computer, a previous test pattern comprising previous regions of previous optical breakdowns; and comparing, by the computer, the test pattern with the previous test pattern to detect a change in threshold energy. The previous test pattern may have been created more than one month ago. The regions of the test pattern may be arranged substantially similarly to the previous regions of the previous test pattern such that each region has a corresponding previous region in the same location. For each region, the laser setting energy that created the region may be substantially the same as the laser setting energy that created the previous region corresponding to the region. The method may also include: providing, by the computer, a notification of the change in the threshold energy; adjusting, by the computer, the laser setting energy to compensate for the change in the threshold energy; and/or extrapolating, by the computer, from the test pattern and the previous test pattern to predict a future threshold energy. The method of claim 11, each region of the test pattern having a substantially rectangular shape or a substantially triangular shape.

In certain embodiments, an ophthalmic surgical system for monitoring incision performance includes a laser device, a camera, and a computer. The laser device delivers a laser beam with a laser setting energy towards a target to create optical breakdowns in the target. The camera generates images of the optical breakdowns in the target. The computer instructs the laser device to create the optical breakdowns in the target to yield a test pattern. The test pattern comprises regions of optical breakdowns, where each region was created with a different laser setting energy and has a substantially rectangular or triangular shape. From the images, the computer identifies a lowest energy region with substantially continuous optical breakdowns, defined as at least 90% of the pulses formed an optical breakdown. The computer designates the laser setting energy used to create the identified region as a threshold energy. The computer also accesses a previous test pattern created more than one month ago comprising previous regions of previous optical breakdowns. The regions of the test pattern arranged substantially similarly to the previous regions of the previous test pattern such that each region has a corresponding previous region in the same location. For each region, the laser setting energy that created the region is substantially the same as the laser setting energy that created the previous region corresponding to the region. The computer compares the test pattern with the previous test pattern to detect a change in threshold energy, provides a notification of the change in the threshold energy, adjusts the laser setting energy to compensate for the change in the threshold energy, and/or extrapolates from the test pattern and the previous test pattern to predict a future threshold energy.

DESCRIPTION OF EXAMPLE EMBODIMENTS

Figure 1:
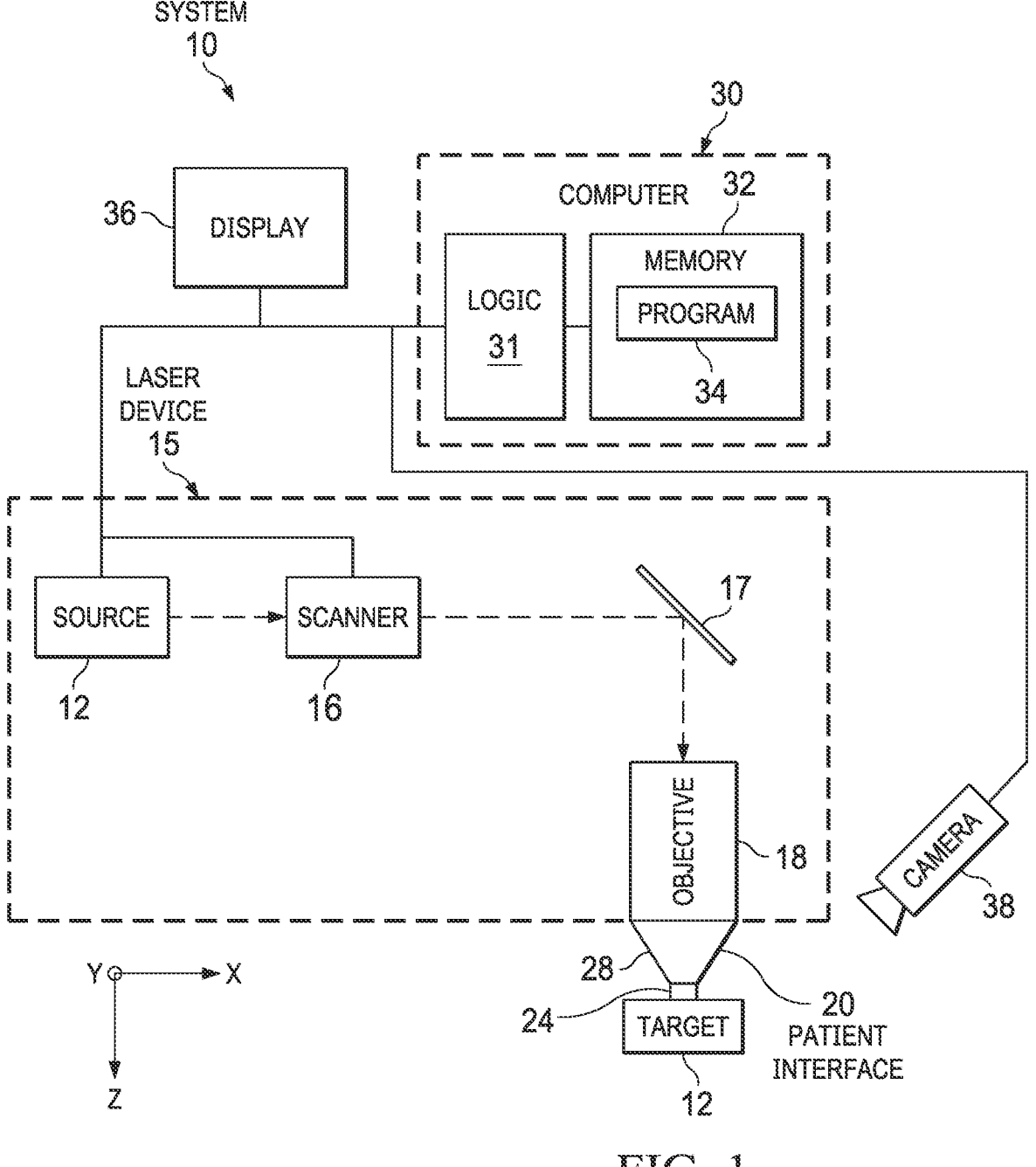
FIG. 1 illustrates an example of an ophthalmic surgical system that can be used to monitor its incision performance, according to certain embodiments.

Referring now to the description and drawings, example embodiments of the disclosed apparatuses, systems, and methods are shown in detail. The description and drawings are not intended to be exhaustive or otherwise limit the claims to the specific embodiments shown in the drawings and disclosed in the description. Although the drawings represent possible embodiments, the drawings are not necessarily to scale and certain features may be simplified, exaggerated, removed, or partially sectioned to better illustrate the embodiments.

Laser surgical systems change over their service life such that a greater laser setting energy may be needed to meet a threshold energy. Embodiments of the system described herein address this issue. In the embodiments, a laser device creates optical breakdowns in a target to yield a test pattern. The test pattern comprises regions of optical breakdowns, where each region is created with a different laser setting energy. A computer identifies a lowest energy region with substantially continuous optical breakdowns, and designates the laser setting energy used to create the identified region as the threshold energy. The computer may compare the test pattern with test patterns made previously to detect changes in the threshold energy and to predict future changes in the threshold energy.

The embodiments provides an efficient, effective, automated determination of incision performance that can be used to identify and predict changes in the threshold energy. Moreover, photodisruptions are influenced by a variety of laser parameters, e.g., beam profile, beam quality, pulse duration, pulse-to-pulse stability, and focusability. The embodiments test the resulting effect of the pulses, which automatically accounts for changes in these parameters.

FIG. 1 illustrates an example of an ophthalmic surgical system 10 that can be used to monitor its incision performance, according to certain embodiments. Ophthalmic surgical system 10 may perform any suitable surgical procedure on an eye 22, such as corneal refractive surgery or other ophthalmic laser surgery. The surgical procedure may have a treatment pattern, which describes the target locations of the laser pulses in the cornea.

In the illustrated example, system 10 includes a laser device 15, a patient interface 20, a camera 38, and a control computer 30, coupled as shown. Laser device 15 includes controllable components, such as a laser source 12, a scanner 16, one or more optical elements 17, and/or a focusing objective 18, controllable by a computer such as computer 30, coupled as shown. Patient interface 20 includes a contact portion 24 (with an abutment face 26) and a sleeve 28 coupled as shown. Computer 30 includes logic 31, a memory 32 (which stores a computer program 34), and a display 36, coupled as shown.

As an overview, computer 30 instructs laser device 15 to create optical breakdowns in a target to yield a test pattern. Laser device 15 delivers a laser beam with energy selected by a laser setting towards target 12 to create the optical breakdowns. The test pattern comprises regions of optical breakdowns, where each region is created with a different laser setting energy. Camera 38 generates images of the optical breakdowns. Computer 30 identifies from the images a lowest energy region with substantially continuous optical breakdowns, and designates the laser setting energy used to create the identified region as the threshold energy.

Going into more detail, target 12 comprises a material that reacts to laser pulses in a way that provides information about how eye tissue reacts to laser pulses. For example, polymethyl methacrylate (PMMA) may operate as a substitute for corneal tissue. Laser pulses below a threshold energy yield no visible reaction, but reactions that exceed the threshold energy yield a visible mark.

Turning to the parts of system 10, laser device 15 includes laser source 12 and scanner 16. Laser source 12 generates a laser beam having ultrashort pulses, where a propagation direction of the laser beam defining a z-axis. Laser source 12 generates a laser beam with ultrashort pulses. An ultrashort pulse refers to a light pulse that has a duration that is less than a nanosecond, such as on the order of picoseconds, femtoseconds, or attoseconds. The laser beam may have any suitable wavelength, such as a wavelength in the range of 300 to 1500 nanometers (nm), e.g., a wavelength in the range of 300 to 650, 650 to 1050, 1050 to 1250, and/or 1250 to 1500 nm, such as 340 to 350 nm, e.g., 347 nm±1 nm. The focal point of the laser beam may create a laser-induced optical breakdown (LIOB) in tissue (e.g., the cornea) to yield a photodisruption in the tissue.

Scanner 16 longitudinally and transversely directs the focal point of the laser beam towards target 12. The longitudinal direction refers to the direction of the laser beam propagation, i.e., the z-direction. Scanner 16 may longitudinally direct the laser beam in any suitable manner. For example, scanner 16 may include a longitudinally adjustable lens, a lens of variable refractive power, or a deformable mirror that can control the z-position of the focal point. The transverse direction refers to directions orthogonal to the direction of beam propagation, i.e., the x- and y-directions. Scanner 16 may transversely direct the laser beam in any suitable manner. For example, scanner 16 may include a pair of galvanometrically-actuated scanner mirrors that can be tilted about mutually perpendicular axes. As another example, scanner 16 may include an electro-optical crystal that can electro-optically steer the laser beam.

One (or more) optical elements 17 direct the laser beam towards focusing objective 18. An optical element 17 can act on (e.g., transmit, reflect, refract, diffract, collimate, condition, shape, focus, modulate, and/or otherwise act on) a laser beam. Examples of optical elements include a lens, prism, mirror, diffractive optical element (DOE), holographic optical element (HOE), and spatial light modulator (SLM). In the example, optical element 17 is a mirror. Focusing objective 18 focuses the focal point of laser beam through the patient interface 20 towards a point of eye 22. In the example, focusing objective 18 is an objective lens, e.g., an f-theta objective.

Patient interface 20 couples target 12 to laser device 15. In the example, patient interface 20 includes sleeve 28 with contact portion 24. Sleeve 28 detachably couples to laser device 15 and target 12. Contact portion 24 may be translucent or transparent to the laser beam.

Camera 38 records images of test patterns created on target 12 and delivers image data, which represent recorded images of target 12, to computer 30. Examples of camera 38 include a video, optical coherence tomography (OCT), or eye-tracking camera. Display 36 displays the images and the results of image analysis performed by computer 30. Examples of display include a computer screen.

Computer 30 controls controllable components of laser device 15 (e.g., laser source 12, scanner 16, optical elements 17, and/or focusing objective 18) in accordance with instructions (which may be stored in computer program 34) to photodisrupt the target to create optical breakdowns that yield test patterns. Computer 30 analyzes the test patterns by, e.g., performing image processing on images of the test pattern from camera 38. Computer 30 also controls camera 38 and display 36 to generate images of the test patterns and display the images and results of the image analysis.

Figure 2A:
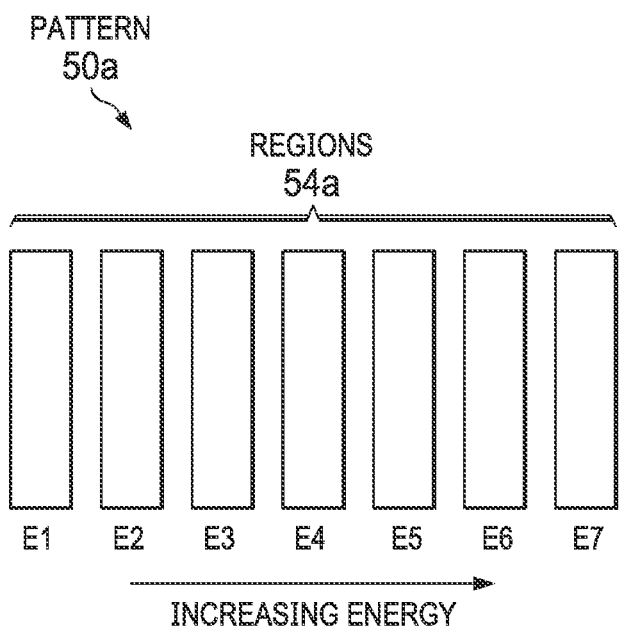
FIGS. 2A and 2B illustrate examples of test patterns.
Figure 2B:
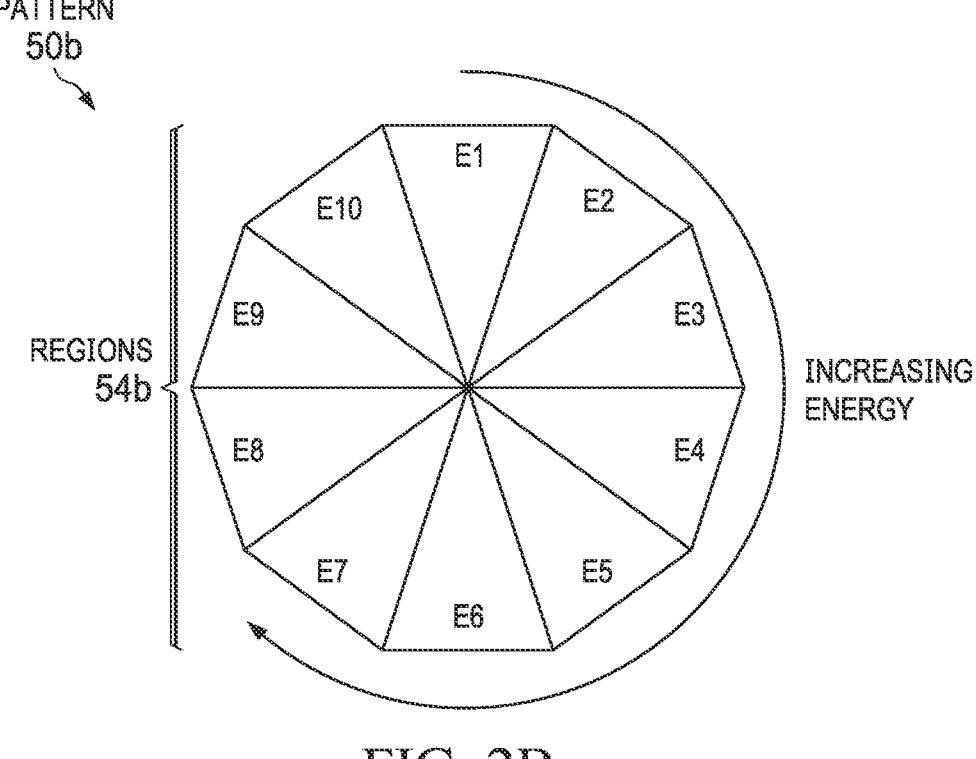

FIGS. 2A and 2B illustrate examples of test patterns 50 (50a, 50b). A test pattern 50 comprises regions 54 of optical breakdowns, where each region was created with a different laser setting energy. In test pattern 50a, each region 54a has a substantially rectangular shape, where pulses with laser setting energies E1 though E7 form optical breakdowns. In test pattern 50b, each region 54b has a substantially triangular shape, where pulses with laser setting energies E1 though E10 form optical breakdowns.

Figure 3A:
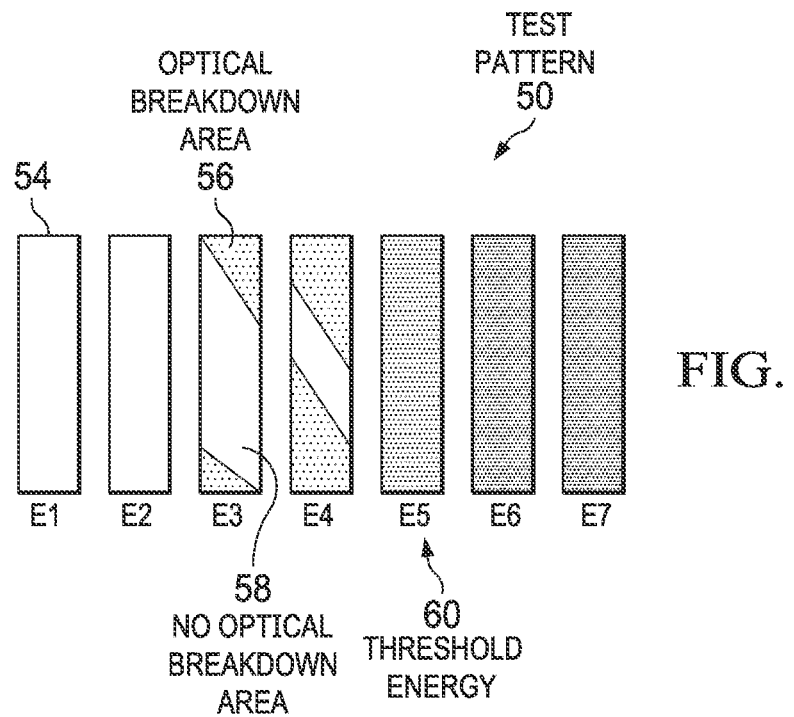
FIGS. 3A and 3B illustrate an example of analyzing a test pattern and comparing the test pattern with a previously made test pattern.
Figure 3B:
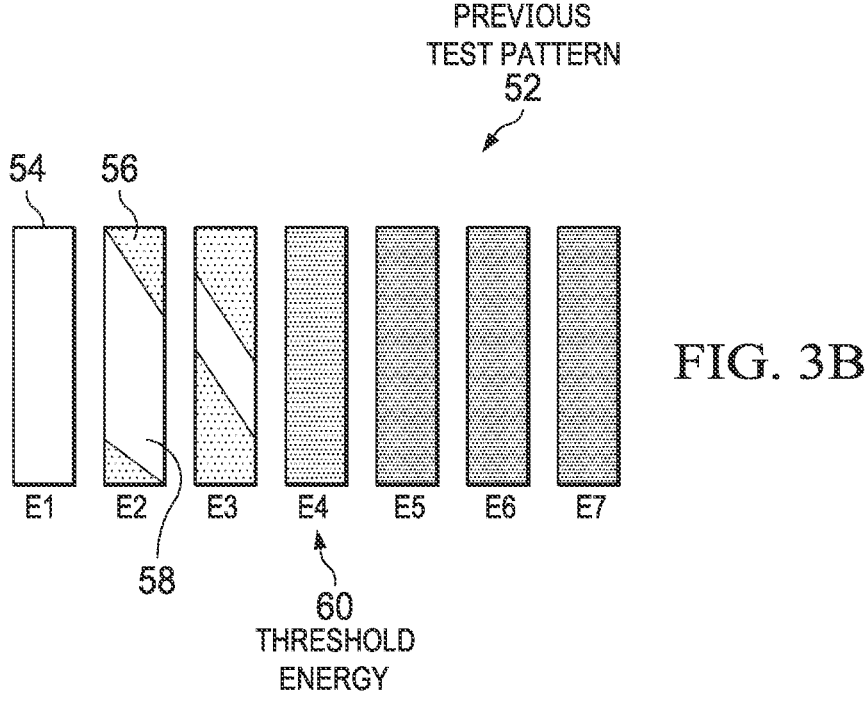

FIGS. 3A and 3B illustrate an example of analyzing a current test pattern 50 made at time T1 and comparing current test pattern 50 with a previous test pattern 52 made at a previous time TO. Test pattern 50 comprises regions 54 of optical breakdowns, where each region 54 was created with a different laser setting energy, E1 through E7. A region 54, e.g., regions E3 and E4, may have areas with optical breakdowns 56 and areas with no optical breakdowns 58. Computer 30 identifies a lowest energy region with substantially continuous optical breakdowns, e.g., region E5. This may be a region where almost all or all of the pulses formed an optical breakdown 56, e.g., where at least 80%, 90%, 95%, 98%, and/or 100% of the pulses formed an optical breakdown. The laser setting energy used to create the identified region is designated as the threshold energy.

In certain embodiments, regions 54 of current test pattern 50 are arranged substantially similarly to regions 54 of previous test pattern 52 such that each current region 54 has a corresponding previous region 54 in the same location. For each region, the laser setting energy, E1 to E7, that created the current region is the same as the laser setting energy, E1 to E7, that created the previous region corresponding to the current region. Test patterns may be created in response to detecting a change in incision quality and/or periodically, where a time period may be in the range of, e.g., 1 month, 1 to 4 months, 4 to 6 months, and/or 6 to 12 months.

Computer 30 may compare current test pattern 50 with previous test pattern 52 for any suitable analysis, e.g., to detect a change in threshold energy. For example, current test pattern 50 indicates that E5 is the threshold energy, whereas previous test pattern 52 indicates that E4 was the previous threshold energy, indicating a change in threshold energy. In certain embodiments, computer 30 may provide a notification of the change in the threshold energy and/or adjust the laser setting energy to compensate for the change in the threshold energy. For example, computer 30 may add the energy difference E5-E4 to the laser energy settings of treatment patterns.

In certain embodiments, computer 30 may extrapolate from current test pattern 50 and previous test pattern 52 to predict a future threshold energy. For example, during the time period T1-T0 between test patterns 50, 52, the energy change E5-E4 occurred. Computer 30 may predict that a similar energy change E5-E4 may occur during the next time period that lasts T1-T0.

Figure 4:
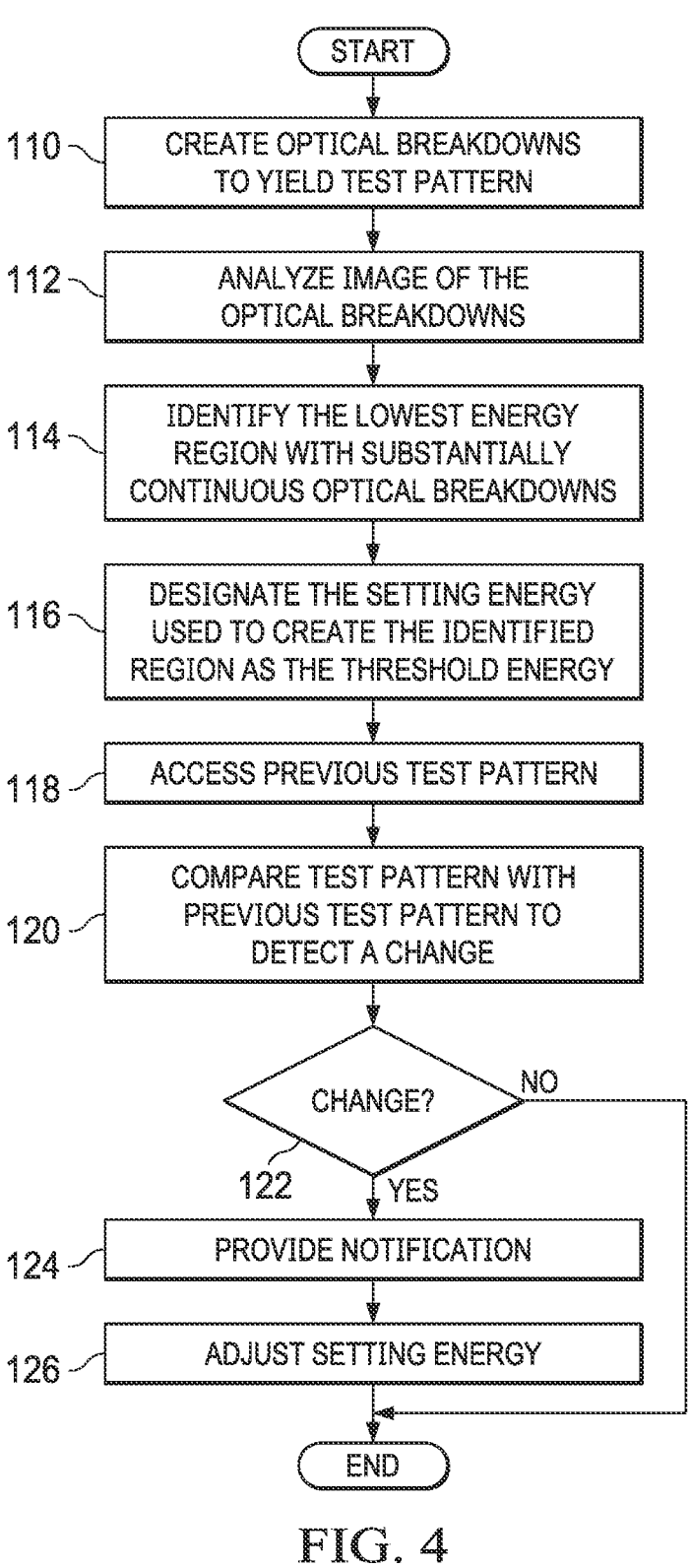
FIG. 4 illustrates an example of a method for checking the incision performance of the system of FIG. 1, according to certain embodiments.

FIG. 4 illustrates an example of a method for monitoring the incision performance of the system of FIG. 1, according to certain embodiments. In the embodiments, a computer of the system performs or instructs other components to perform the steps of the method. The method starts at step 110, where the laser device of the system delivers a laser beam to a target to create optical breakdowns that yield a test pattern. The test pattern has regions of optical breakdowns, where each region was created with a different laser setting energy.

The computer analyzes images of the optical breakdowns recorded by a camera at step 112. The computer identifies the lowest energy region with substantially continuous optical breakdowns at step 114. The region with substantially continuous optical breakdowns may be a region where at least almost all of the pulses formed an optical breakdown. The laser setting energy used to create the identified region is designated as the threshold energy at step 116.

The computer accesses a previous test pattern at step 118. The computer compares the current test pattern with the previous test pattern at step 120 to detect a change in the threshold energy. There may be a change at step 122. If there is no change, the method ends. If there is a change, the computer provides a notification of the change in energy at step 124. For example, the computer may display a notification on display 36 of the change in energy, along with a description of the change (e.g., the current and previous values of the threshold energy). The computer adjusts laser setting energy to compensate for the changes at step 126. For example, the computer may add the change in energy to the laser energy settings of treatment patterns. The method then ends.

A component (such as computer 30) of the systems and apparatuses disclosed herein may include an interface, logic, and/or memory, any of which may include computer hardware and/or software. An interface (such as display 36) can receive input to the component and/or send output from the component, and is typically used to exchange information between, e.g., software, hardware, peripheral devices, users, and combinations of these. A user interface is a type of interface that a user can utilize to communicate with (e.g., send input to and/or receive output from) a computer. Examples of user interfaces include a display, Graphical User Interface (GUI), touchscreen, keyboard, mouse, gesture sensor, microphone, and speakers.

Logic can perform operations of the component. Logic may include one or more electronic devices that process data, e.g., execute instructions to generate output from input. Examples of such an electronic device include a computer, processor, microprocessor (e.g., a Central Processing Unit (CPU)), and computer chip. Logic may include computer software that encodes instructions capable of being executed by an electronic device to perform operations. Examples of computer software include a computer program, application, and operating system.

A memory can store information and may comprise tangible, computer-readable, and/or computer-executable storage medium. Examples of memory include computer memory (e.g., Random Access Memory (RAM) or Read Only Memory (ROM)), mass storage media (e.g., a hard disk), removable storage media (e.g., a Compact Disk (CD)

or Digital Video or Versatile Disk (DVD)), database, network storage (e.g., a server), and/or other computer-readable media. Particular embodiments may be directed to memory encoded with computer software.

Although this disclosure has been described in terms of certain embodiments, modifications (such as changes, substitutions, additions, omissions, and/or other modifications) of the embodiments will be apparent to those skilled in the art. Accordingly, modifications may be made to the embodiments without departing from the scope of the invention. For example, modifications may be made to the systems and apparatuses disclosed herein. The components of the systems and apparatuses may be integrated or separated, or the operations of the systems and apparatuses may be performed by more, fewer, or other components, as apparent to those skilled in the art. As another example, modifications may be made to the methods disclosed herein. The methods may include more, fewer, or other steps, and the steps may be performed in any suitable order, as apparent to those skilled in the art.

To aid the Patent Office and readers in interpreting the claims, Applicants note that they do not intend any of the claims or claim elements to invoke 35 U.S.C. § 112(f), unless the words "means for" or "step for" are explicitly used in the particular claim. Use of any other term (e.g., "mechanism," "module," "device," "unit," "component," "element," "member," "apparatus," "machine," "system," "processor," or "controller") within a claim is understood by the applicants to refer to structures known to those skilled in the relevant art and is not intended to invoke 35 U.S.C. § 112(f).

What is claimed:

1. An ophthalmic surgical system for monitoring incision performance, comprising:
   a laser device configured to deliver a laser beam with a laser setting energy towards a target, the laser beam creating a plurality of optical breakdowns in the target;
   a camera configured to generate a plurality of images of the optical breakdowns in the target; and
   a computer configured to:
      instruct the laser device to create the optical breakdowns in the target to yield a test pattern, the test pattern comprising a plurality of regions of optical breakdowns, each region created with a different laser setting energy;
      identify from the images a lowest energy region with substantially continuous optical breakdowns; and
      designate the laser setting energy used to create the identified region as a threshold energy.

2. The ophthalmic surgical system of claim 1, the substantially continuous optical breakdowns defined as at least 90% of the pulses formed an optical breakdown.

3. The ophthalmic surgical system of claim 1, the computer further configured to:
   access a previous test pattern comprising a plurality of previous regions of previous optical breakdowns; and
   compare the test pattern with the previous test pattern to detect a change in threshold energy.

4. The ophthalmic surgical system of claim 3, the previous test pattern created more than one month ago.

5. The ophthalmic surgical system of claim 3, the computer further configured to:
   provide a notification of the change in the threshold energy.

6. The ophthalmic surgical system of claim 3, the computer further configured to:

adjust the laser setting energy to compensate for the change in the threshold energy.

7. The ophthalmic surgical system of claim 3, the computer further configured to:
   extrapolate from the test pattern and the previous test pattern to predict a future threshold energy.

8. The ophthalmic surgical system of claim 3:
   the regions of the test pattern arranged substantially similarly to the previous regions of the previous test pattern such that each region has a corresponding previous region in the same location; and
   for each region, the laser setting energy that created the region is substantially the same as the laser setting energy that created the previous region corresponding to the region.

9. The ophthalmic surgical system of claim 1, each region of the test pattern having a rectangular shape.

10. The ophthalmic surgical system of claim 1, each region of the test pattern having a triangular shape.

11. A method for monitoring incision performance, comprising:
   instructing, by a computer, a laser device to deliver a laser beam with a laser setting energy towards a target, the laser beam creating a plurality of optical breakdowns in the target to yield a test pattern, the test pattern comprising a plurality of regions of optical breakdowns, each region created with a different laser setting energy;
   generating, by a camera, a plurality of images of the optical breakdowns in the target; identifying, by the computer, from the images a lowest energy region with substantially continuous optical breakdowns; and
   designating, by the computer, the laser setting energy used to create the identified region as a threshold energy.

12. The method of claim 11, the substantially continuous optical breakdowns defined as at least 90% of the pulses formed an optical breakdown.

13. The method of claim 11, further comprising:
   accessing, by the computer, a previous test pattern comprising a plurality of previous regions of previous optical breakdowns; and
   comparing, by the computer, the test pattern with the previous test pattern to detect a change in threshold energy.

14. The method of claim 13, the previous test pattern created more than one month ago.

15. The method of claim 13, further comprising:
   providing, by the computer, a notification of the change in the threshold energy.

16. The method of claim 13, further comprising:
   adjusting, by the computer, the laser setting energy to compensate for the change in the threshold energy.

17. The method of claim 13, further comprising:
   extrapolating, by the computer, from the test pattern and the previous test pattern to predict a future threshold energy.

18. The method of claim 13:
   the regions of the test pattern arranged substantially similarly to the previous regions of the previous test pattern such that each region has a corresponding previous region in the same location; and
   for each region, the laser setting energy that created the region is substantially the same as the laser setting energy that created the previous region corresponding to the region.

19. The method of claim 11, each region of the test pattern having a substantially rectangular shape or a substantially triangular shape.

\* \* \* \* \*